United States Patent [19]

Bonetta et al.

[11] Patent Number: 4,534,365
[45] Date of Patent: Aug. 13, 1985

[54] APPARATUS FOR EVALUATING FOOT CONDITION

[75] Inventors: Angelo A. Bonetta, Niagara Falls, Canada; Bruno R. Galiotto, Verona, Italy

[73] Assignee: Canadian Ursus Rubber Limited, Niagara Falls, Canada

[21] Appl. No.: 597,043

[22] Filed: Apr. 5, 1984

[51] Int. Cl.³ .............................................. A61B 5/10
[52] U.S. Cl. ................................... 128/779; 272/144; 108/23; 177/177; 73/172
[58] Field of Search ........................ 128/774, 779, 736; 108/23; 272/144–146; 177/177; 356/445; 73/172

[56] References Cited

U.S. PATENT DOCUMENTS

| | | | |
|---|---|---|---|
| 2,009,340 | 7/1935 | Edwards | 128/779 |
| 2,096,615 | 10/1937 | MacDonald et al. | 128/779 |
| 2,325,490 | 7/1943 | Elftman | 128/779 X |
| 2,382,131 | 8/1945 | Cameron | 128/779 X |
| 2,480,361 | 8/1949 | Doumitt | 128/779 |
| 3,311,070 | 3/1967 | Barzee et al. | 108/23 |
| 3,894,437 | 7/1975 | Hagy et al. | 128/779 X |
| 3,993,809 | 11/1976 | Schranz et al. | 128/736 X |
| 4,267,728 | 5/1981 | Manley et al. | 128/779 X |
| 4,302,971 | 12/1981 | Luk | 374/162 |
| 4,379,461 | 4/1983 | Nilsson et al. | 128/736 |
| 4,416,293 | 11/1983 | Anderson et al. | 128/779 X |
| 4,467,727 | 8/1984 | Strommer | 108/23 |

FOREIGN PATENT DOCUMENTS 2517008 11/1975 Fed. Rep. of Germany ........ 73/172

OTHER PUBLICATIONS

Cavanagh et al.; "Tech. for Display of Press. Distrib. Beneath the Foot"; *J. Biomechanics*, vol. 13, No. 2, 1980, pp. 69–75.

*Primary Examiner*—Lee S. Cohen
*Assistant Examiner*—Angela D. Sykes
*Attorney, Agent, or Firm*—Sim & McBurney

[57] ABSTRACT

Apparatus for evaluating a person's foot condition in terms of blood circulation in and anatomical shape of the feet has a transparent planar foot support with a thermographic film provided thereon to visually indicate the degree of blood circulation in the foot. The foot support is mounted on a stand with lamps for illuminating the underside of the foot support. Mirrors are positioned on the stand beneath the foot support to enable unobstructed viewing of the visual indication. By rotating the mirror, a camera may be used to photograph the visual indication of the person's foot condition. The apparatus provides an economic unit for use in readily evaluating a person's foot condition.

14 Claims, 6 Drawing Figures

APPARATUS FOR EVALUATING FOOT CONDITION

FIELD OF THE INVENTION

This invention relates to apparatus for evaluating a person's blood circulation in and anatomical shape of their feet.

BACKGROUND OF THE INVENTION

Thermographic apparatus has been used for diagnosing the degree of blood circulation in the limbs of people. For example, U.S. Pat. No. 4,379,461 discloses a thermographic apparatus which uses an infrared detector carried on a linkage which is moved along the patient's limb to determine the temperature profile along the limb in evaluating the circulation in the limb. However, that device has not been adapted for use in evaluating the circulation in a person's foot. Although there are very costly computerized devices for evaluating blood circulation, they are not usable in the field such as shoe stores or any other facility concerned with orthopedic examination where an inexpensive but reliable source in evaluating foot shape and blood circulation is required, so that the proper shoe and/or treatment can be prescribed for the customer.

Devices, which have been used in evaluating the anatomical shape of a person's foot, are disclosed in U.S. Pat. Nos. 2,009,340, 2,096,615, 2,325,490, 2,382,131 and 2,480,361. U.S. Pat. No. 2,325,490 discloses a stand having a transparent foot support of glass with a slanted mirror located beneath the foot support. A camera is positioned exterior of the stand and the mirror angled relative to the foot support to permit photographing the shape of the person's foot in evaluating the physical pressure points of the foot. Another foot visualizer is disclosed in U.S. Pat. No. 2,382,131. A dual mirror arrangement is provided to enable viewing of the person's foot shape and characteristics from above the unit. A similar device is disclosed in U.S. Pat. No. 2,480,361 where elongate lamps are provided beneath the foot stand to illuminate and thereby show to the viewer the condition of the person's foot.

Liquid crystal temperature indicators have been used in measuring human body temperatures as disclosed in U.S. Pat. Nos. 3,993,809 and 4,302,971. A special film construction is provided in U.S. Pat. No. 3,993,809 to provide elasticity in the film for location on contoured parts of the body so that the film may be flexed and thereby conformed to provide proper indication of body temperature. To alleviate this problem, U.S. Pat. No. 4,302,971 discloses liquid crystal temperature indicator which is of a reduced size so that it may be readily located on the planar portion of the person's forehead to indicate body temperature.

The apparatus, according to this invention, provides an economical arrangement which readily indicates the condition of the person's foot to assist the user in selecting proper foot wear and/or treatment to improve foot condition. Because of its simplicity and economy in manufacture, the device can be readily used in most normal shoe stores or orthopedic shoe stores and other centres which evaluate foot condition.

SUMMARY OF THE INVENTION

According to an aspect of the invention, the apparatus for evaluating a person's foot condition in terms of blood circulation and/or anatomical shape of their feet comprises a transparent planar foot support mounted on a stand, where the underside of the foot support is illuminated. The foot support and stand are adapted to receive and support a device on which a barefooted person stands to indicate visually the condition of the person's feet. A mirror system is mounted beneath the foot support to enable unobstructed viewing of the underside of the transparent foot support. A camera is mounted on the stand and the mirror system includes a rotatably mounted mirror on the stand for rotation about an axis parallel with the plane of the foot support. A first stop means is provided to angle the rotatable mirror relative to the mirror system for unobstructed viewing. A second stop means is provided to angle the rotatable mirror when rotated from the first stop means to permit photographing by the camera of the visual indication by the device of the person's foot condition.

According to an aspect of the invention, the device for visually indicating the foot condition of a person standing on the device comprises a temperature responsive liquid crystal composition in a durable film. The liquid crystal composition visually indicates various temperature ranges by a corresponding color array.

BRIEF DESCRIPTION OF THE DRAWINGS

Preferred embodiments of the invention are shown in the drawings wherein.

DETAILED DESCRIPTION OF THE PREFERRED EMBODIMENTS

Figure 1:
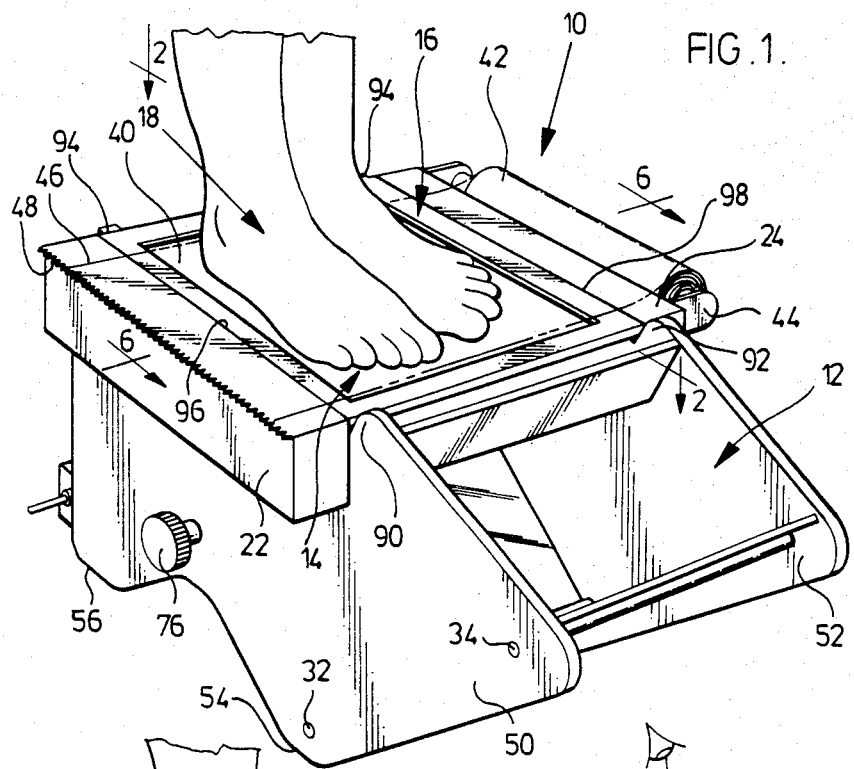
FIG. 1 is a perspective view of a preferred embodiment of the apparatus according to this invention.
Figure 2:
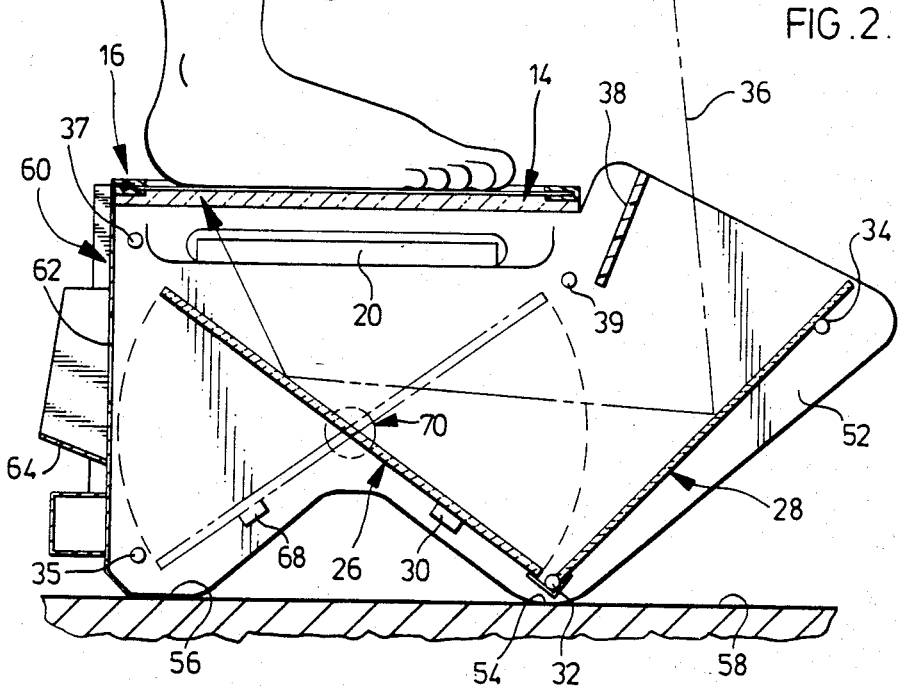
FIG. 2 is a planar side view of a section taken along lines 2—2 of FIG. 1 with the mirrors arranged to provide for visual viewing.

The apparatus 10, as shown in FIG. 1, comprises a stand 12 for a transparent foot support 14 which is shown more clearly in FIG. 2. A device 16 is placed on top of the foot support which is a film adapted to indicate visually the degree of blood circulation in the person's feet 18. The device 16 is temperature responsive and indicates by a color array the varying temperatures across the profile of the person's feet 18. It is understood that the varying temperatures are caused by varying blood circulation in the foot. The higher the degree of blood circulation, the warmer that portion of the foot is.

Lamps 20, as shown in FIG. 2 and contained in enclosures 22 and 24 on each side of the stand, illuminate the underside of the foot support 14 so that the color array of device 16 can be visually inspected.

To facilitate visual inspection by either the person standing on the apparatus 10 or by a person standing beside the apparatus, a mirror system, according to this embodiment, comprises a first mirror 26 and a second mirror 28. With the mirror 26 in the first position as defined by first stop 30 and the mirror 28 in the fixed position as defined by cross-members 32 and 34 of the stand 12, a person may view the complete underside of the transparent foot 14 along the line of view 36. To facilitate such viewing, a shield 38 is provided to prevent glare from lamps 20 reflecting off the mirror 28, thereby obscuring viewing of the underside of the foot support 14.

To provide for sanitary conditions on the device 16, a sheet of paper 40 is drawn across the device 16 so that the person stands on the paper 40 which is in direct contact with the thermographic device 16, thereby providing a direct heat transfer between the person's feet and the device 16. The paper 40 is withdrawn from supply role 42 which is mounted on standards 44. The paper is fed beneath tear-bar 46 which is provided with a jagged edge 48 to permit tearing off paper 40 which has previously been used.

Figure 3:
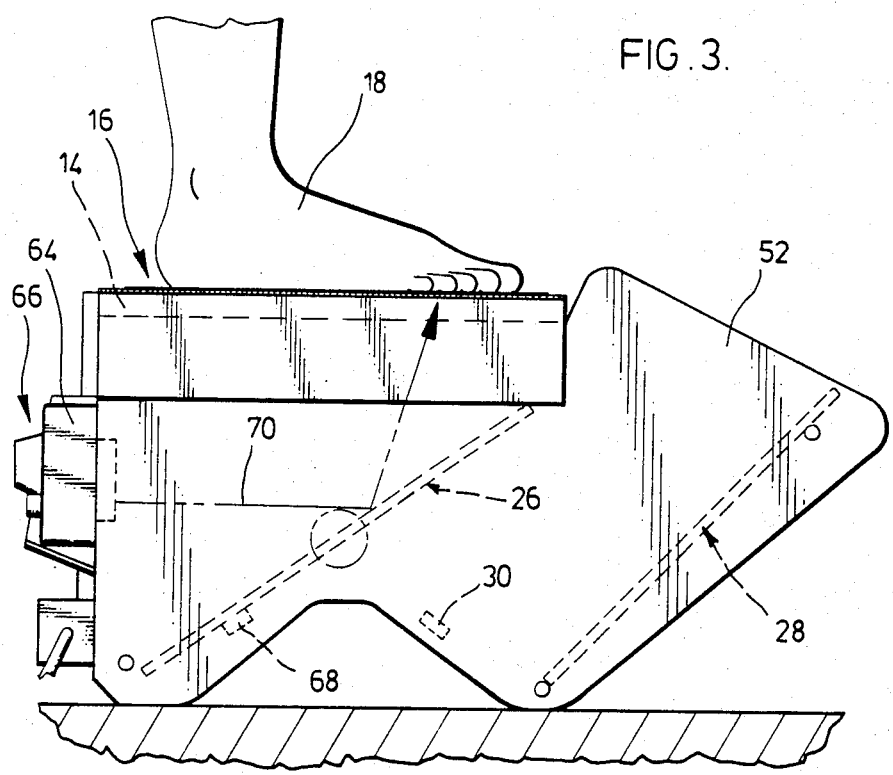
FIG. 3 shows the mirror arrangement of FIG. 2 in a second position to enable photographing the visual indication of foot condition.

The stand 12 comprises opposing parallel side panels 50 and 52. The side panels are joined by cross-members 32, 34, 35, 37 and 39 as shown in FIG. 2. By securing these cross-members in the side panels 50 and 52, a secured stand is provided to support the weight of an individual whose foot condition is being evaluated. In additon, the shield 38 further rigidifies the stand as it interconnects the side members 50 and 52. Foot portions 54 and 56 which rest on the floor surface 58 are shown in FIG. 2. The stand includes an end panel 60 which interconnects and spans the space between the sides 50 and 52. The end panel includes an aperture 62, as more clearly shown in FIG. 5, along with a shell 64 to which a camera 66, as shown in FIG. 3, is mounted. With the mirror 26 in the second position against stop 68, the line of sight is depicted by arrow 70. With the appropriate focal length on camera 66, the complete underside of the foot support 14 may be photographed to record the visual indication by device 16 of the person's foot condition.

Figure 6:
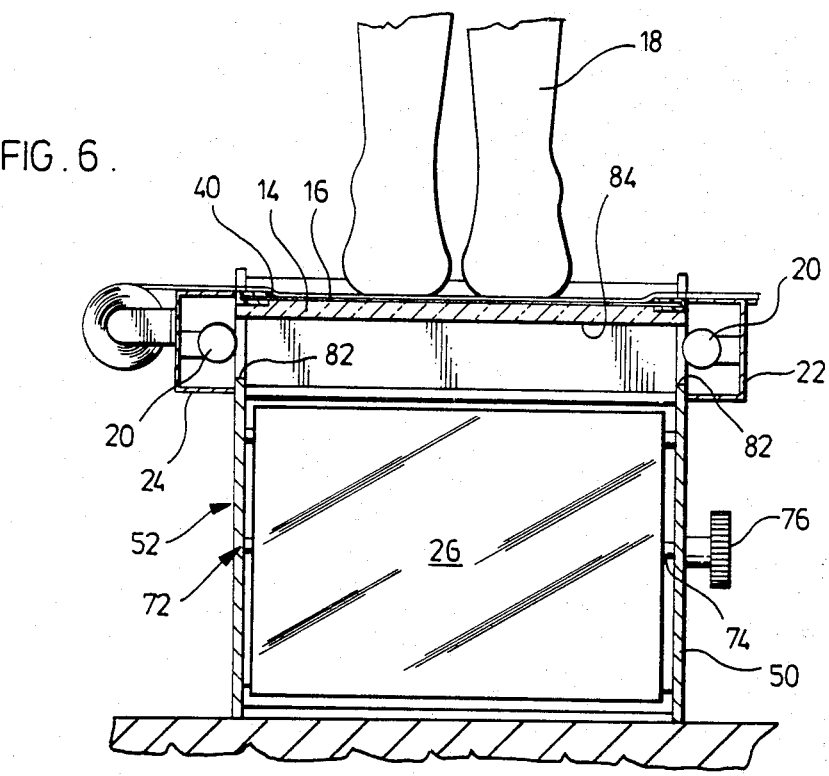
FIG. 6 is a section taken along lines 6—6 of FIG. 1.

To provide for rotation of the mirror 26 so that the user may selectively position the mirror to facilitate viewing along sight line 36 as shown in FIG. 2, or photographing the visual indication along sight line 70 as shown in FIG. 3, the mirror 26 is mounted on an axle indicated at 70. The first end of the axle is rotatably mounted in side 52 at bearing 72 as shown in FIG. 6. The other end 74 extends through a bearing in side wall 50 and to which a knob 76 is secured. By manually grasping knob 76, the mirror 26 may be rotated from a first position, as defined by stop 30, to a second positon as defined by stop 68. This arrangement thereby provides in a single arrangement by way of rotatable mirror 26 the advantage of either viewing or photographing the readout from the device for sensing and indicating circulation of blood in the customer's foot. The camera 66 may be of the "Polaroid" (trademark) type which may be manually actuated or actuated by remote control. The camera is removable from the shell 64 to permit reloading with film.

It is understood that the mirror system may have many different configurations and components. For example, a single mirror may be used such that when in a first position, its angle still permits viewing by the user stooping over the apparatus and looking at the mirror. By positioning the rotatable single mirror in the second position, the camera may be used.

Figure 5:
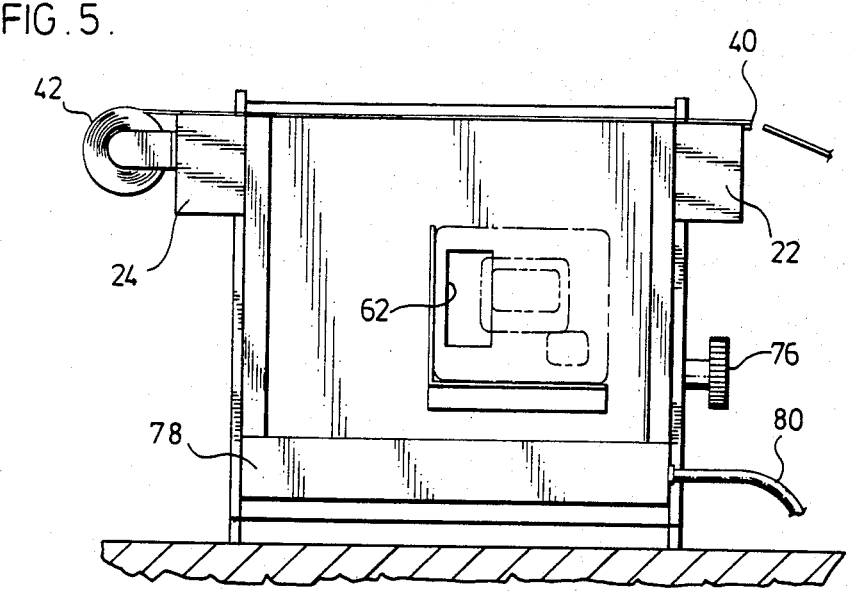
FIG. 5 is an end view of the apparatus of FIG. 1 with the camera mounted thereon.

As shown in FIG. 5, electrical connector box 78 is provided into which electrical cord or wiring 80 passes. Within the electrical box 78 is a junction which electrically connects lamps 20 on each side of the apparatus, as shown in FIG. 6, to the electrical wiring 80. A switch may be optionally provided either on the electrical box 78 or in the electrical cord 80 to turn the lamps 20 "off" and "on". Otherwise the lamps are controlled by simply plugging the electrical wiring 80 into an appropriate wall socket. In FIG. 6, the side panels 50 and 52 have slots 82 cut therein to allow the light from lamps 20 to illuminate the underside 84 of the foot support 14.

Figure 4:
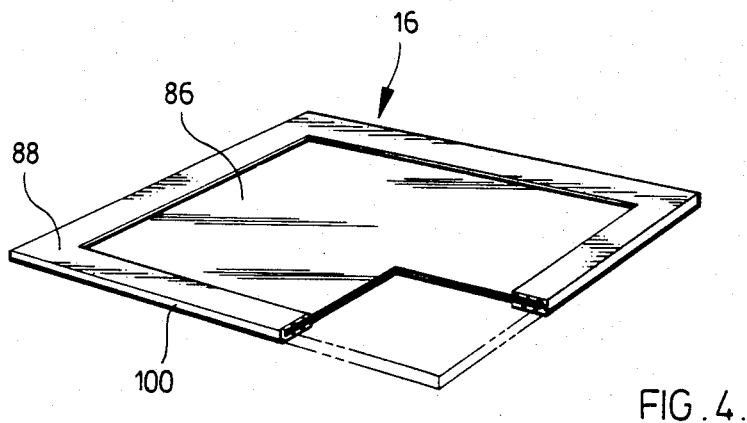
FIG. 4 is a perspective view of the device for visually indicating the degree of blood circulation in the foot.

As shown in FIG. 4, the thermographic film 86 of the thermographic device 16 is mounted in a frame 88. The stand 12 provides abutments 90, 92 and 94 on the front and rear portions of the sides 50 and 52. The lamp enclosures 22 and 24 provide abutment portions 96 and 98 along the sides of the foot support to thereby retain the device 16 on the foot support 14 by the abutments cooperating with the frame edges 100.

The thermographic film is made of a durable construction to withstand daily use, the paper 40 providing additional protection for the film. The film 86 comprises an upper layer of black opaque material and an intermediate layer of a temperature sensitive substance which may be a cholesteric liquid crystal compound which produces a visible color change in response to a temperature activation. The crystal make up is such to respond in providing temperature gradients for the temperature range of normally healthy feet having proper blood circulation. This temperature range is from approximately 25° C. to approximatley 45° C. when measured at an ambient temperature approximating room temperature, namely 23° C.

The intermediate crystal layer is protected on its underside by a transparent film. Thus the person standing on device 16 does not see from the upper surface any reaction of the film 86. The color spectrum is visible only from the underside of the foot support. Depending upon the temperature gradient of the foot, the corresponding color array is indicated. For normally healthy feet, the film 86 will respond in a manner to show reasonably consistent temperature reading along the length of the foot. For feet with poor circulation, the color gradient will indicate a lower temperature along the foot by a different color array. For a particular cholesteric make up used, the following colors indicate the degree of blood circulation in the foot. A deep blue indicates good blood circulation, green indicates fair blood circulation, brown indicates poor blood circulation and no color indicates very poor blood circulation.

Since the foot support 14 is a hard surface, the color array will also outline the anatomical shape of the individual's foot to indicate the height of the arch and the pressure points of the feet. Therefore, the person evaluating the customer's blood circulation will also determine simultaneously the condition of the person's foot profile. This information, therefore, permits the salesperson or orthopedic specialists to select the appropriate footwear or treatment to improve foot condition.

By way of photographing the visual indication of the person's foot condition, a record may be kept on the customer so that on return with further use of the apparatus, the improvement in the customer's foot condition can be observed and then the next proper set of footwear or treatment prescribed.

The foot support plate 14 is preferably of "Plexiglass" (trademark) or may be of other transparent material. Thick plateglass is least preferred because it is subject to breakage and its additional weight.

Although various preferred embodiments of the invention have been described herein in detail, it will be understood by those skilled in the art that variations may be made thereto without departing from the spirit of the invention or the scope of the apperided claims.

THE EMBODIMENTS OF THE INVENTION IN WHICH AN EXLUSIVE PROPERTY OR PRIVILEGE IS CLAIMED ARE DEFINED AS FOLLOWS:

1. Apparatus for evaluating a person's foot condition in terms of blood circulation in and/or anatomical shape of their feet comprising a transparent planar foot support mounted on a stand, said foot support having an upper surface, means for illuminating the underside of said transparent foot support, said foot support and stand receiving and supporting a device on which a barefooted person is adapted to stand indicating visually the condition of the feet of a person adapted to be standing on said device, a mirror system mounted beneath said foot support to enable unobstructed viewing of the underside of said transparent foot support by a person standing adjacent said stand, means for mounting a camera on said stand, said mirror system having a mirror rotatably mounted on said stand for rotation about an axis parallel with the plane of said foot support, a first stop means to angle said rotatable mirror in a first position for viewing and second stop means to angle said rotatable mirror in a second position when isolated from said first stop means relative to a camera when present in said camera mounting means to enable photographing the visual indication of a person's foot condition.

2. Apparatus of claim 1, wherein said mirror system comprises a first mirror which is said rotatable mirror and a second mirror which is mounted on said stand and fixed, said first mirror in said first position providing viewing via said second mirror.

3. Apparatus of claim 2, wherein said first mirror includes metallic portions for contacting said first and second stop means which each have a magnetic portion thereby positively retaining said first mirror in either of its viewing or photographing positions.

4. Apparatus of claim 2 or 3, wherein said first mirror is secured to an axle, said stand having means for mounting said axle parallel to the plane of said planar foot support, a handle secured to said axle and extending from said axle mounting means to permit manual rotation of said first mirror to the first or second positions.

5. Apparatus of claim 2, wherein said stand comprises spaced-apart parallel planar sides with interconnecting cross-members to secure the stand, said foot support being rectangular and mounted on and bridging the spaced-apart stand sides, said first mirror being rectangular and secured to an axle mounted in said sides to provide thereby an unobstructed area between said foot support and said first mirror, said second mirror being rectangular and secured to opposing portions of said sides.

6. Apparatus of claim 5, wherein an end wall spans and is secured to opposing portions of said stand sides wall, said end wall being mounted opposite said second mirror, said camera mounting means being provided in said end wall.

7. Apparatus of claim 1, 2 or 5, wherein said transparent foot support is of rigid transparent plastic.

8. Apparatus of claim 2, 3 or 5, wherein said first mirror rotates approximately 110 degrees between said first and second positions and the angle between said first mirror when at said first position and said second mirror is approximately 100 degrees.

9. Apparatus of claim 2, 3 or 5, wherein said first mirror in said first position enables viewing of the visual indication of foot circulation from above said apparatus.

10. Apparatus of claim 1, said device for visually indicating the foot condition of a person standing on said device comprises a temperature-responsive liquid crystal composition in a durable film, said liquid crystal composition visually indicating various temperature ranges by a corresponding color array, said illumination means illuminating said color array to facilitate viewing or photographing.

11. Apparatus of claim 10, wherein said illumination means comprises two spaced-apart parallel lamps extending along opposite sides of and beneath said foot support.

12. Apparatus of claim 1, 2 or 10, wherein means for mounting a roll of paper is provided on said stand adjacent a side of said foot support, paper being paid off from said roll across the upper surface of said foot support, means for tearing paper which has been laid across said foot support provided along a side of said foot support opposite said paper roll mounting means.

13. Apparatus of claim 5, wherein said film is mounted in a frame, abutments provided about the perimeter of said foot suppoprt which abut the perimeter of said film frame to center and retain said film on said foot support.

14. Apparatus of claim 5, wherein the outline of the color array indicates the anatomical shape of the person's foot.

* * * * *